(12) United States Patent
Van Heesch et al.

(10) Patent No.: US 10,369,386 B2
(45) Date of Patent: Aug. 6, 2019

(54) ULTRASOUND TRANSDUCER FOR SELECTIVELY GENERATING ULTRASOUND WAVES AND HEAT

(75) Inventors: Christianus Martinus Van Heesch, Eindhoven (NL); Aleksey Kolesnychenko, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 666 days.

(21) Appl. No.: 13/699,027

(22) PCT Filed: May 24, 2011

(86) PCT No.: PCT/IB2011/052255
§ 371 (c)(1),
(2), (4) Date: Nov. 20, 2012

(87) PCT Pub. No.: WO2011/148314
PCT Pub. Date: Dec. 1, 2011

(65) Prior Publication Data
US 2013/0066240 A1  Mar. 14, 2013

(30) Foreign Application Priority Data

May 27, 2010 (EP) .................................... 10164111

(51) Int. Cl.
*A61N 7/02* (2006.01)
*G01N 29/34* (2006.01)
(Continued)

(52) U.S. Cl.
CPC ............... *A61N 7/022* (2013.01); *A61N 7/02* (2013.01); *G01N 29/34* (2013.01); *A61B 8/00* (2013.01);
(Continued)

(58) Field of Classification Search
CPC ...................................................... A61B 18/08
(Continued)

(56) References Cited

U.S. PATENT DOCUMENTS 5,267,985 A * 12/1993 Shimada ........... A61M 37/0092
                                                    601/2
5,460,595 A * 10/1995 Hall ....................... A61B 8/546
                                                    310/316.01
(Continued)

FOREIGN PATENT DOCUMENTS

EP          0370801 A1 *  5/1990  ............... G01H 9/00
JP         2002153480 A     5/2002
(Continued)

OTHER PUBLICATIONS

R Seip, E Ebbini, "Noninvasive Estimation of Tissue Temperature Response to Heating Fields Using Diagnostic Ultrasound", 1995, IEEE Transactions on Biomedical Engineering, vol. 42, No. 8, pp. 828-839.*

(Continued)

*Primary Examiner* — James M Kish

(57) ABSTRACT

An ultrasound transducer is configured to be driven at multiple frequencies including a main frequency for efficient production of ultrasound waves and at least one alternative frequency, at which little or no ultrasound is generated and rather heat is generated in the ultrasound transducer for heating a sample.

20 Claims, 2 Drawing Sheets

(51) Int. Cl.
*A61B 8/00* (2006.01)
*A61N 7/00* (2006.01)

(52) U.S. Cl.
CPC ............... *A61N 2007/0039* (2013.01); *A61N 2007/0073* (2013.01)

(58) Field of Classification Search
USPC .......................................................... 601/2
See application file for complete search history.

(56) References Cited

U.S. PATENT DOCUMENTS

| | | |
|---|---|---|
| 5,522,869 A | 6/1996 | Burdette et al. |
| 5,601,526 A | 2/1997 | Chapelon et al. |
| 6,334,846 B1 | 1/2002 | Ishibashi et al. |
| 6,440,725 B1 | 8/2002 | Pourahmadi et al. |
| 7,521,023 B2 | 4/2009 | Garrison |
| 8,568,339 B2 | 10/2013 | Rybyanets |
| 2002/0128639 A1* | 9/2002 | Pless ............... A61B 17/2202 606/27 |
| 2003/0036706 A1* | 2/2003 | Slayton ............... A61B 5/01 600/439 |
| 2004/0082857 A1 | 4/2004 | Schonenberger et al. |
| 2005/0182326 A1* | 8/2005 | Vilkomerson ................. 600/439 |
| 2006/0084891 A1 | 4/2006 | Barthe et al. |
| 2006/0206105 A1 | 9/2006 | Chopra et al. |
| 2006/0253026 A1 | 11/2006 | Gueck et al. |
| 2008/0091104 A1* | 4/2008 | Abraham ....................... 600/439 |
| 2008/0139974 A1* | 6/2008 | Da Silva ................. A61B 8/546 601/3 |
| 2008/0248554 A1* | 10/2008 | Merchant et al. ............ 435/259 |
| 2009/0041833 A1* | 2/2009 | Bettinger et al. .............. 424/450 |
| 2010/0182877 A1* | 7/2010 | Chu ............................... 367/140 |
| 2011/0087096 A1* | 4/2011 | Behar ............................ 600/438 |
| 2011/0178407 A1* | 7/2011 | Lu et al. ........................ 600/459 |
| 2012/0182877 A1 | 7/2012 | Kailash |
| 2013/0096595 A1 | 4/2013 | Myhr et al. |

FOREIGN PATENT DOCUMENTS

| | | |
|---|---|---|
| WO | WO2008070580 | 6/2008 |
| WO | WO2009095894 | 8/2009 |
| WO | WO 2010009141 A1 * | 1/2010 |
| WO | WO2011071703 | 6/2011 |
| WO | WO2011075227 | 6/2011 |
| WO | 2011092683 A1 | 8/2011 |

OTHER PUBLICATIONS

Journal of Internal Medicine, "Chapter III: The Effects of Ultrasound on Tissues and Organs in Animals and Humans". Acta Medica Scandinavica, vol. 170, Issue S369, Jan./Dec. 1961, pp. 23-32.*

Form 2906—Office Action—EP counterpart of SN 13699027.

* cited by examiner

ULTRASOUND TRANSDUCER FOR SELECTIVELY GENERATING ULTRASOUND WAVES AND HEAT

FIELD OF THE INVENTION

The invention relates to the field of ultrasound transducers, and in particular to ultrasound transducers for selectively generating ultrasound waves and heat for use in analysis and/or diagnostics.

BACKGROUND OF THE INVENTION

Since long, ultrasound is used in the field of medical treatment. Recently, ultrasonic transducers, in particular high intensity focused ultrasound transducers, have been used for inducing lesions in tissue for therapeutic cancer treatment. Tissue lesion or tissue destruction is caused by cavitation effects of high intensity ultrasonic waves. This cavitation effect is linked to the formation of microscopic vapor bubbles in a region, where the pressure of liquid falls below its vapor pressure. When these bubbles collapse, energy is released leading to the destruction of neighboring tissue.

U.S. Pat. No. 5,601,526 describes a method and an apparatus for performing therapy using ultrasound for tissue disruption by means of cavitation and thermal effects. This document is concerned with providing a solution allowing a lesion in tissue to be treated, which is strictly limited to the focus point of the treatment device, and limiting or avoiding effects due to heat spreading around the focus point, with cavitation phenomena being limited exclusively to the focal point or to the focal region. For this, two types of ultrasonic waves are employed, one producing predominantly a thermal effect on the tissue, the other producing predominantly a cavitation effect on the tissue. Here, heating in the tissue occurs due to absorption of ultrasonic energy by frictional damping.

Also in analysis and diagnostics, ultrasound is more and more employed. For instance, the detection of infectious pathogens for prevention, early diagnosis and treatment of infectious diseases are based on the analysis of intracellular components, e.g. nucleic acids or specific molecules, of viruses or cells in a sample. Thus, one of the processing steps before analyzing the components is cell-lysis (cell breaking). Cell-lysis can be induced by means of high intensity focused ultrasound waves that generate cavitations in the sample. Upon implosion of these cavitations, enough energy is released to destroy the membranes of bacteria, viruses and cells and release their intracellular components.

Moreover, working with cells or small organisms involves a thorough control of environmental conditions, such as temperature. Temperature has wide influence, for instance, on the metabolism and the reproduction cycle of bacteria and cells. Hence, for most biological applications, temperature control is required. Yet, the space for adding more components to an experimental setup, such as heating means, is extremely limited, and in particular, since the trend is to minimize the sample volume for saving material costs and for accelerating the procedures. Therefore, a compact setup design is desirable.

However, when heating is performed due to ultrasonic energy absorption of a high intensity focused ultrasonic beam, the sample may be unintentionally influenced or sensitive components in a sample, such as membranes, may be damaged by local pressure and/or temperature peaks in the sample. In particular, it may be required to heat the sample before ultrasonic treatment without exposing the sample to acoustic pressure waves in order to get neat results. Thus, in diagnostics and analysis, it is often required to heat a sample without potentially manipulating or damaging it. Therefore, ways for gently heating a sample in a controlled way have to be found, being at the same time cost saving, space saving, easy to control and sufficiently fast.

SUMMARY OF THE INVENTION

Hence, it is an object of the invention to provide heating means for an ultrasonic application setup, capable of heating a sample gently and fast and being cost and space saving.

The object is solved by the features of the independent claims. The basic idea of the invention is based on the finding that an ultrasound transducer can be driven at several drive frequencies, whereof usually only the lowest one efficiently generates ultrasonic waves. At other frequencies, almost no ultrasonic intensity is emitted; instead the transducer itself heats up. Therefore, it is proposed to use an ultrasound transducer for selectively providing ultrasound and heat to a sample. For this, an ultrasound transducer is used that can be operated at different frequencies. For ultrasound application, the ultrasound transducer is operated at a main frequency, at which ultrasonic waves are generated very efficiently. For heating, the ultrasound transducer is operated at an alternative frequency, at which the transducer heats up.

Preferably, the main and alternative frequencies are resonance frequencies of the ultrasound transducer or close to those. The frequency, at which ultrasonic waves are most efficiently generated, is the main resonance frequency, while at other resonance frequencies; much less ultrasonic energy is emitted. Using resonance frequencies as driving frequencies, the supplied electrical energy is most efficiently transformed by the ultrasound transducer. However, it may not always be advantageous to use the exact resonance frequency, but rather a frequency close to it. The frequency, at which the ultrasound transducer is driven, may be adjustable by means of a control unit. It is then preferable that a user interface is provided, so that a user can select certain frequencies and adjust also other experimental parameters, e.g. intensity of emitted ultrasound, set-point temperature or heating rate.

In one exemplary embodiment, the main frequency for generating ultrasonic waves is lower than at least one of the alternative frequencies used for heating. In particular, the main frequency may be the lowest resonance frequency of the ultrasound transducer. It is preferred that high intensity ultrasonic waves can be generated at the main frequency. In one embodiment, these high intensity ultrasonic waves are capable of creating cavitations in a sample or in a liquid medium. By means of cavitations, lysis of cells, bacteria, virus capsules or membrane compartments may be induced. Preferably, the ultrasound transducer only generates ultrasound waves of sufficiently high intensity, when it is driven at the main frequency. Alternatively, the main frequency may represent the frequency, at which the highest intensity of ultrasonic waves is generated. In another example, the ultrasound intensity emitted at at least one of the alternative frequencies is much lower than the ultrasound intensity emitted at the main frequency. By these means, the alternative frequency can be used for heating without employing stress by acoustic pressure waves.

In one embodiment, at least one of the alternative frequencies is more efficient with respect to heating than the main frequency. Heat may be produced in the ultrasound transducer due to electric power absorption of the ultrasound transducer at one or more of the alternative resonance frequencies. Preferably, driving the ultrasound transducer at one of the alternative frequencies can be adjusted for heating such that either no ultrasonic waves are generated at all or at least none capable of creating cavitation effects. The heating characteristics, e.g. rate of temperature increase or maximum temperature, may vary among the alternative frequencies of the ultrasound transducer. Therefore, preferably, an appropriate alternative frequency can be selected by a user among the plurality of alternative frequencies, e.g. depending on the maximum temperature to be reached or on the desired rate of temperature increase. The heating characteristics of the alternative frequencies may be stored in some storing means and may be indicated to the user.

In a further embodiment, the ultrasound transducer is capable of being driven simultaneously at at least two frequencies or is capable of switching continuously between frequencies. Thus, the ultrasound transducer may be driven at the main as well as at one of the alternative frequencies, so that the sample may be heated, while high intensity ultrasonic waves are induced. Therefore, it is preferred that the main frequency and at least one of the alternative frequencies suitable for heating are drivable independently from each other. This is to say that all parameters of driving the ultrasound transducer, e.g. intensity, period, interval, amplitude, coordinates of focus point etc., can be adjusted for each frequency separately. Possibly, this can be realized by using an ultrasound transducer having several separate piezoelectric elements or the like.

In another embodiment of the invention, a system for sample analysis is proposed. The system preferably comprises at least one sample holder and at least one ultrasound transducer, wherein the ultrasound transducer corresponds to any of the above-mentioned embodiments. The sample analysis may include DNA diagnostics, detection of infectious pathogens and/or diagnosis and treatment of infectious diseases. For this, the system may comprise all conventional components for performing these tasks, for instance a microcontroller or computer, display means, analysis means, a control unit, a microscope and so on. Preferably, the inventive system may be incorporated in an existing setup, e.g. in a lab-on-a-chip system.

In a preferred embodiment, the system also comprises temperature control and/or temperature sensing means. Instead of temperature sensing means, however, also an ultrasound transducer may be used that is capable of measuring the sample temperature based on sound velocity measurements. It may moreover be useful to employ a feedback cycle for the temperature control. In addition, the sample holder is preferably designed such that it is able to provide good heat conduction between the ultrasound transducer and the sample. In this regard, also heat conductive paste or the like may be employed. At the same time, of course, good acoustic coupling should be provided. By these means, it can be ensured, that the generated ultrasonic waves as well as the generated heat can be coupled into the sample without considerable loss.

In a further embodiment of the invention, a method for controlling an ultrasound transducer or sample analysis is proposed. This method comprises the steps of controlling an ultrasound transducer at a main frequency for efficiently generating ultrasonic waves and/or at one of at least one alternative frequency for heating a sample. Preferably, this method is used for operating an ultrasound transducer according to one of the above-described embodiments. In one embodiment, almost no ultrasonic waves are produced, when driving the ultrasound transducer at at least one of the alternative frequencies. Moreover, heating should be performable simultaneously to ultrasound wave generation. Thus, it should be possible to drive the ultrasound transducer simultaneously at at least two different frequencies, i.e. at the main frequency and one alternative frequency. In addition, it is preferred that the temperature of the sample is controlled and/or monitored. Possibly, also a feedback cycle for controlling the temperature of the sample is realized.

BRIEF DESCRIPTION OF THE DRAWINGS

These and other aspects of the invention will be apparent from and elucidated with reference to the embodiments described hereinafter and illustrated by the drawings.

DETAILED DESCRIPTION OF EMBODIMENTS

For enabling heating as well as treating with ultrasound, an ultrasound transducer is used that can be driven at at least two different frequencies. One of these frequencies should be adapted for the efficient generation of ultrasonic waves, whereas the other frequency should result in heating up the ultrasound transducer, almost without generation of ultrasonic waves. Various types of ultrasonic transducers may be employed, such as piezoelectric ultrasound transducers or capacitive micro-machined ultrasound transducers. Preferably, high intensity focused ultrasound transducers (HIFU-transducers) are employed that are able to focus the ultrasonic beam to a small focal region in a sample. It is also preferred to use resonance frequencies for driving the ultrasound transducer, in order to ensure a favorable transformation ratio of input electrical energy to output energy. However, in some cases, it may be preferable to use frequencies close to a resonance frequency, multitudes of a resonance frequency or the like. Hence, instead of resonance frequencies, also other driving frequencies may be used.

Figure 1A:
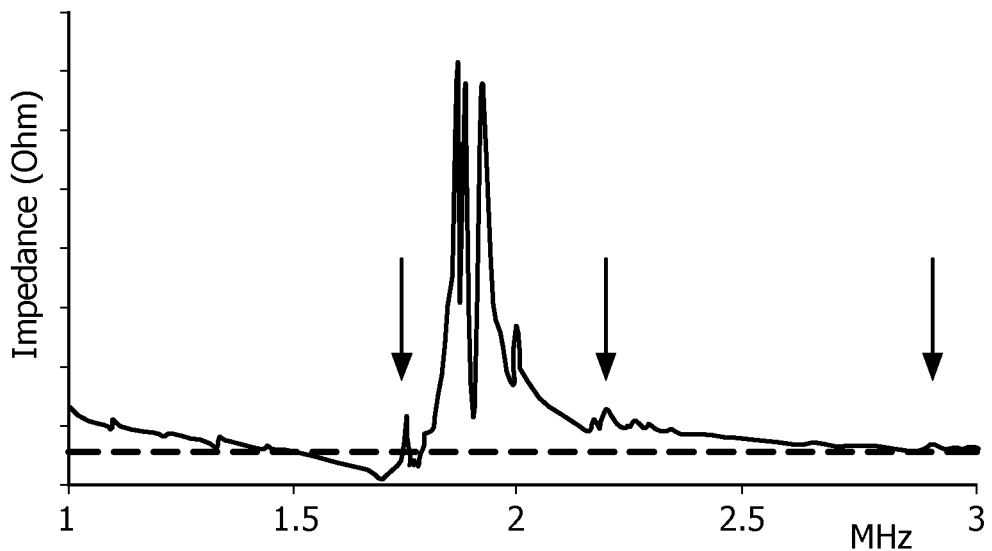
FIG. 1A shows an exemplary impedance spectrum of an exemplary ultrasound transducer.

Usually, an ultrasound transducer efficiently generates ultrasonic waves only at its main resonance frequency. At other alternative resonance frequencies, much less or almost no ultrasonic waves are generated. In FIG. 1A, an exemplary impedance spectrum of an ultrasound transducer is shown. The ultrasound transducer has several resonance frequencies, e.g. the main resonance frequency centered at about 1.7 MHz, and alternative resonance frequencies centered at about 2.17 MHz and 2.86 MHz (arrows). The main resonance frequency is a fundamental vibration mode of a piezo-electric element of the ultrasound transducer. These alternative resonance frequencies can represent bending modes of the piezo-electric element or higher harmonics. At these frequencies, the ultrasound transducer heats up quickly.

Around 1.9 MHz, the impedance increases and fluctuates a lot, as shown in FIG. 1A. This is due to the method of measuring the impedance and a result of electrical reflections and resonances. Due to the high impedance, a lot of electric signal is reflected back to the amplifier resulting in this kind of artifacts in the measurement.

At an impedance about 50 Ohm (dashed line), all electrical equipment works optimal with no electrical reflection.

When the impedance of the ultrasound transducer is 50 Ohm (e.g. at 1.52 MHz), the ultrasound transducer does not heat up as fast as at resonance frequencies, 'proving' the heating is due to the resonance, not due to electric power. The main resonance frequency at 1.7 MHz is at 50 Ohm as well.

Figure 1B:
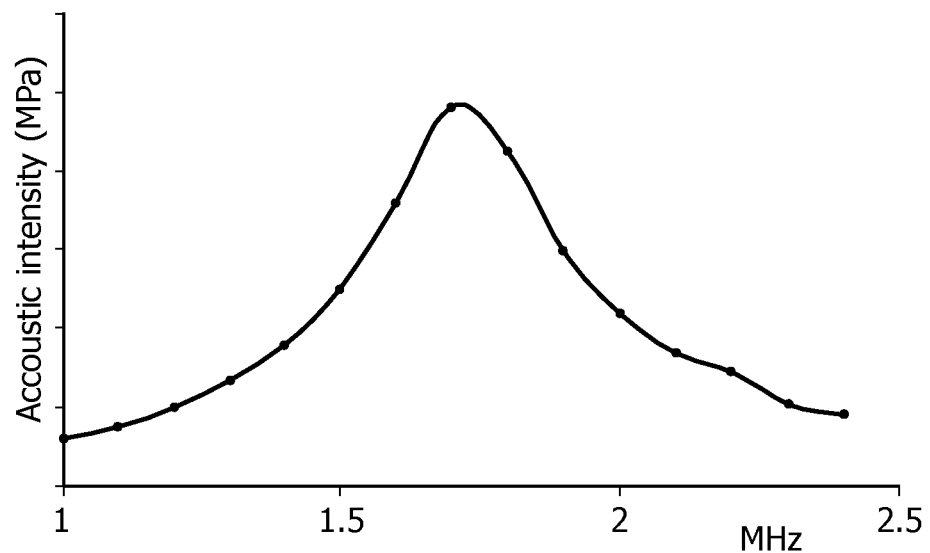
FIG. 1B displays the ultrasound intensity emitted by the ultrasound transducer in dependency on the driving frequencies.

Furthermore, FIG. 1B shows an exemplary relation of emitted ultrasound intensity and driving frequency of the ultrasound transducer. Thus, the ultrasound transducer predominantly emits ultrasound waves at its main resonance frequency, in this example at 1.7 MHz. At all other frequencies, much less ultrasonic intensity is emitted, but the absorbed electrical energy is merely transformed into heat in the ultrasound transducer.

According to the invention, the ultrasound transducer can be controlled to operate at an ultrasound generating main frequency and at a heat generating alternative frequency. Hence, the transducer may be selectively used to apply acoustic pressure waves to the sample or as a heating plate for heating the sample. Usually, the main frequency is lower than most of the alternative frequencies. If resonance frequencies are used, it may even be the lowest resonance frequency. At the main frequency, the ultrasound transducer should be capable to produce high intensity ultrasonic waves for creating cavitations, which induce bacteria or cell lysis in the sample. In contrast, the ultrasound intensity generated by driving the ultrasound transducer at one of the alternative frequencies should be much lower and preferably insufficient for inducing cavitation effects.

The parameters of the ultrasound transducer may be adjustable. This may be performed by the user via a user interface or pre-programmed by a control unit. In particular, coordinates of a focus point, intensity, frequency, amplitude, etc. may be adjusted. Furthermore, it may be selected to apply ultrasonic pulses, with adjustable pulse width, period and intervals. If the ultrasound transducer is drivable in more than one alternative frequency, the alternative frequencies may differ in their heating characteristics with respect to ultrasound generation, heating velocity and achievable maximum temperature. Therefore, the alternative frequencies should be selectable according to the requirements of different applications.

In a preferred embodiment, the ultrasound transducer can be driven at two different frequencies simultaneously and independently. Thus, heating and ultrasound generation can be performed at the same time. For instance, this can be achieved with a transducer comprising at least two ultrasound-generating elements, e.g. two piezoelectric elements. One of these elements may be operable at least at the main frequency and capable of generating ultrasound waves, while the other may be operable at one or more alternative frequencies for generating heat. Preferably, the elements are adjustable independently from each other.

Figure 2:
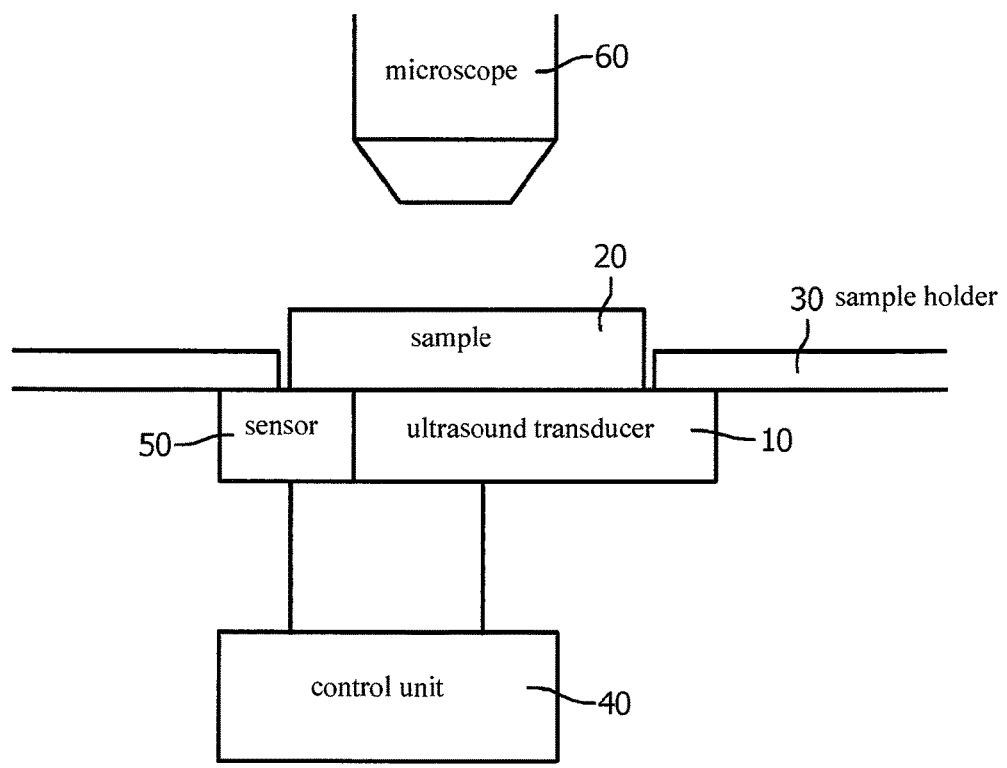
FIG. 2 is a schematic view of a system for sample analysis according to the invention.

In FIG. 2, an example of a system for sample analysis is shown. The system comprises an ultrasound transducer 10 and a sample holder 30 for holding a sample 20. The sample holder 30 is adapted to receive a sample 20 comprised in a Petri dish, a test tube, a slide, or the like. The ultrasound transducer 10 is arranged such that ultrasonic waves as well as heat can efficiently be coupled into the sample 20. In order to improve ultrasonic or thermal conduction, heat conductive paste or ultrasound gel can be used.

In a preferred embodiment, the system further comprises a control unit 40 and a temperature sensor 50. The temperature sensor 50 can be any kind of temperature sensing means and is arranged close to or within the sample 20. In order to further reduce the size of the setup, the ultrasound transducer 10 may also be capable of measuring the sample temperature. For instance, this can be done by measuring the speed of sound in a liquid sample, since the speed of sound in a fluid strongly depends on the temperature of the fluid. The ultrasound transducer 10 may additionally be used for analyzing, e.g. for determining the density or consistency of the sample 20. Moreover, the system may be combined with a microscope 60 in order to image the sample 20 using fluorescence and/or reflected light microscopy.

Preferably, a sample 20 can be heated from 20° C. room temperature to 95° C. within less than two minutes. The heating process may be adjusted by controlling heating cycles at at least one selected alternative frequency, by adjusting intervals between heating cycles, a cycle period or the intensity. Possibly, the transducer 10 can be simultaneously driven at several alternative frequencies for heating, so that also the spectrum of driving frequencies can be adjusted. The heating process may be controlled by the control unit 40 based on data provided by the temperature sensor 50 for regulating the sample temperature in a kind of feedback cycle.

The system may additionally comprise a computer or microcontroller, display means, a memory for storing setup data or measurement data, user interfaces and the like. The system may also be integrated in a general analysis or diagnostic system, for example in a microscopic or other imaging setup, in a lab-on-a-chip system or in a microfluidic system.

By using an ultrasound transducer not only for generating ultrasound waves, but also for other functions, in particular for heating, the setup of an analysis/diagnosis system and the number of setup components may be reduced, thus reducing costs.

The invention claimed is:

1. A method of operating an ultrasound transducer for analysis of a sample, comprising acts of:
providing the ultrasound transducer capable of being operated using at least two frequencies including a main frequency and at least one alternative frequency; and
controlling the ultrasound transducer to operate
at the main frequency for generating ultrasound waves to primarily couple ultrasound waves into the sample; and
at one alternative frequency of the at least one alternative frequency to primarily generate heat in the ultrasound transducer for heating the ultrasound transducer for heating the sample by thermal conduction of the heat from the heated ultrasound transducer to the sample, wherein an impedance of the ultrasound transducer at the one alternative frequency is greater than the impedance at the main frequency to generate the heat in the ultrasound transducer based on the increased impedance of the ultrasound transducer at the one alternative frequency.

2. The method of claim 1, wherein the main frequency and the one alternative frequency are resonance frequencies of the ultrasound transducer.

3. The method of claim 1, wherein when driving the ultrasound transducer with set parameters at at least one of the alternative frequencies, less ultrasound intensity is generated than when driving the ultrasound transducer with the set parameters at the main frequency.

4. The method according to claim 1, wherein ultrasound intensity generated when driving the ultrasound transducer with set parameters at the one alternative frequency is not sufficient for generating cavitations in the sample.

5. The method according to claim 1, wherein the ultrasound waves generated at the main frequency with set parameters are capable of creating the cavitations in the sample.

6. The method according to claim 1, wherein the heat in the ultrasound transducer is generated due to electric power absorption of the ultrasound transducer, when driving the ultrasound transducer at the one alternative frequency.

7. The method according to claim 1, wherein one of the at least one alternative frequency produces more of the heat in the ultrasound transducer than the main frequency.

8. The method according to claim 1, wherein the one alternative frequency is higher than the main frequency.

9. The method according to claim 1, further comprising acts of:
monitoring a temperature of the sample to obtain a monitored temperature; and
controlling the temperature of the sample based on monitored temperature.

10. The method according to claim 1, wherein the controlling act operates the ultrasound transducer simultaneously using the main frequency and the one alternative frequency.

11. The method of claim 1, wherein the controlling act operates the ultrasound transducer alternately using the main frequency and the one alternative frequency.

12. The method of claim 1, further comprising acts of:
storing heating characteristics of the at least one alternative frequency; and
providing the heating characteristics to a user.

13. The method of claim 1, wherein the main frequency is centered at 1.7 MHz, and the at least one alternative frequency centered at 2.17 MHz and 2.86 MHz.

14. The method of claim 1, further comprising an act of measuring a temperature of the sample using the ultrasound transducer by measuring a speed of sound in a fluid of the sample.

15. The method of claim 1, wherein the controlling act operates the ultrasound transducer simultaneously at the one alternative frequency and at a second alternative frequency of the at least one alternative frequency for regulating the heat in the ultrasound transducer.

16. An ultrasound transducer comprising:
a transducer element; and
a controller configured to selectively drive the transducer element using a main frequency to primarily generate ultrasound waves for emission from the transducer element, and to selectively drive the transducer element using at least one alternative frequency different from the main frequency to primarily generate heat in the ultrasound transducer for heating the ultrasound transducer for transfer of the heat by thermal conduction from the heated ultrasound transducer to a sample, wherein an impedance of the ultrasound transducer at the at least one alternative frequency is greater than the impedance at the main frequency to generate the heat in the ultrasound transducer based on the increased impedance of the ultrasound transducer at the at least one alternative frequency.

17. The ultrasound transducer of claim 16, wherein the ultrasound waves are configured to induce cell lysis in the sample.

18. The ultrasound transducer of claim 16, wherein the controller is further configured to alternately drive the transducer element using the main frequency and the at least one alternative frequency.

19. The ultrasound transducer of claim 16, further comprising a further transducer element, wherein the controller is configured to simultaneously drive the transducer element using the main frequency and drive the further transducer element using the at least one alternative frequency.

20. A system for sample analysis, comprising:
at least one sample holder; and
at least one ultrasound transducer having a transducer element and a controller configured to selectively drive the transducer element using a main frequency to primarily generate ultrasound waves for emission from the transducer element, and to selectively drive the transducer element using at least one alternative frequency different from the main frequency to primarily generate heat in the ultrasound transducer for heating the ultrasound transducer,
wherein the ultrasound transducer is heat-conductively coupled to a sample inserted in the at least one sample holder for transfer of the heat by thermal conduction from the heated ultrasound transducer to the sample, wherein an impedance of the ultrasound transducer at the at least one alternative frequency is greater than the impedance at the main frequency to generate the heat in the ultrasound transducer based on the increased impedance of the ultrasound transducer at the at least one alternative frequency.

* * * * *